(12) United States Patent
Specht

(10) Patent No.: US 9,032,614 B2
(45) Date of Patent: May 19, 2015

(54) METHOD FOR MANUFACTURING AN ELECTRICAL BUSHING FOR AN IMPLANTABLE MEDICAL DEVICE

(75) Inventor: Heiko Specht, Hanau (DE)

(73) Assignee: Heraeus Precious Metals GmbH & Co. KG, Hanau (DE)

(*) Notice: Subject to any disclaimer, the term of this patent is extended or adjusted under 35 U.S.C. 154(b) by 378 days.

(21) Appl. No.: 13/361,411

(22) Filed: Jan. 30, 2012

(65) Prior Publication Data

US 2012/0197327 A1      Aug. 2, 2012

Related U.S. Application Data

(60) Provisional application No. 61/438,063, filed on Jan. 31, 2011.

(30) Foreign Application Priority Data

Jan. 31, 2011   (DE) .................. 10 2011 009 862

(51) Int. Cl.
| | |
|---|---|
| H01K 3/22 | (2006.01) |
| H01R 13/52 | (2006.01) |
| A61N 1/375 | (2006.01) |
| H01R 43/20 | (2006.01) |

(52) U.S. Cl.
CPC ............ H01R 13/5224 (2013.01); *H01R 43/20* (2013.01); *H01R 2201/12* (2013.01); A61N 1/3754 (2013.01)

(58) Field of Classification Search
CPC .......... H01R 13/5224; H01R 2201/12; H01R 43/20; A61N 1/3754
USPC ........ 29/25.41, 830–832, 840, 842, 846, 852; 174/257, 264; 419/6, 57; 607/115, 116
See application file for complete search history.

(56) References Cited

U.S. PATENT DOCUMENTS

| | | |
|---|---|---|
| 3,979,187 A | 9/1976 | Scherer |
| 4,152,540 A | 5/1979 | Duncan et al. |

(Continued)

FOREIGN PATENT DOCUMENTS

| | | |
|---|---|---|
| DE | 69729719 | 7/2005 |
| DE | 102006054249 | 5/2008 |

(Continued)

OTHER PUBLICATIONS

The Office Action for U.S. Appl. No. 13/361,322 mailed date Feb. 19, 2014 (26 pages).

(Continued)

*Primary Examiner* — Donghai D Nguyen
(74) *Attorney, Agent, or Firm* — Dicke, Billig & Czaja, PLLC

(57) ABSTRACT

One aspect relates to an electrical bushing for use in a housing of an implantable medical device. The electrical bushing includes at least one electrically insulating base body and at least one electrical conducting element. The electrical bushing includes a holding element to hold the electrical bushing in or on the housing. The conducting element is set-up to establish, through the base body, at least one electrically conductive connection between an internal space of the housing and an external space. The conducting element is hermetically sealed with respect to the base body. The at least one conducting element includes at least one cermet. The holding element is made, to at least 80% by weight with respect to the holding element, from a material selected from the group consisting of a metal from any of the subgroups IV, V, VI, VIII, IX, and X of the periodic system.

9 Claims, 5 Drawing Sheets

(56) References Cited

U.S. PATENT DOCUMENTS

| | | | |
|---|---|---|---|
| 4,217,137 A | 8/1980 | Kraska et al. | |
| 4,315,054 A | 2/1982 | Sack et al. | |
| 4,354,964 A | 10/1982 | Hing et al. | |
| 4,488,673 A | 12/1984 | Hopper, Jr. | |
| 4,602,956 A * | 7/1986 | Partlow et al. | 419/57 |
| 4,678,868 A | 7/1987 | Kraska et al. | |
| 4,991,582 A | 2/1991 | Byers et al. | |
| 5,043,535 A | 8/1991 | Lin | |
| 5,515,604 A | 5/1996 | Horine et al. | |
| 5,769,874 A | 6/1998 | Dahlberg | |
| 5,861,714 A | 1/1999 | Wei et al. | |
| 5,870,272 A | 2/1999 | Seifried et al. | |
| 6,093,476 A | 7/2000 | Horiuchi et al. | |
| 6,414,835 B1 | 7/2002 | Wolf et al. | |
| 6,643,903 B2 | 11/2003 | Stevenson et al. | |
| 6,660,116 B2 | 12/2003 | Wolf et al. | |
| 6,999,818 B2 | 2/2006 | Stevenson et al. | |
| 7,035,076 B1 | 4/2006 | Stevenson | |
| 7,038,900 B2 | 5/2006 | Stevenson et al. | |
| 7,136,273 B2 | 11/2006 | Stevenson et al. | |
| 7,145,076 B2 | 12/2006 | Knappen et al. | |
| 7,174,219 B2 | 2/2007 | Wahlstrand et al. | |
| 7,260,434 B1 | 8/2007 | Lim et al. | |
| 7,274,963 B2 | 9/2007 | Spadgenske | |
| 7,437,817 B2 | 10/2008 | Zhang et al. | |
| 7,480,988 B2 | 1/2009 | Ok et al. | |
| 7,502,217 B2 | 3/2009 | Zhao et al. | |
| 7,561,917 B2 | 7/2009 | Wegrzyn, III et al. | |
| 7,564,674 B2 | 7/2009 | Frysz et al. | |
| 7,630,768 B1 | 12/2009 | Coffed et al. | |
| 7,706,124 B2 | 4/2010 | Zhao et al. | |
| 7,720,538 B2 | 5/2010 | Janzig et al. | |
| 7,736,191 B1 | 6/2010 | Sochor | |
| 7,742,817 B2 | 6/2010 | Malinowski et al. | |
| 7,747,321 B2 | 6/2010 | Fischbach et al. | |
| 7,761,165 B1 | 7/2010 | He et al. | |
| 7,765,005 B2 | 7/2010 | Stevenson | |
| 7,794,256 B1 | 9/2010 | Sochor | |
| 7,901,761 B1 * | 3/2011 | Jiang et al. | 174/264 |
| 7,930,032 B2 | 4/2011 | Teske et al. | |
| 7,989,080 B2 | 8/2011 | Greenberg et al. | |
| 8,000,804 B1 | 8/2011 | Wessendorf et al. | |
| 8,065,009 B2 | 11/2011 | Biggs | |
| 8,131,369 B2 | 3/2012 | Taylor et al. | |
| 8,163,397 B2 | 4/2012 | Ok et al. | |
| 8,288,654 B2 | 10/2012 | Taylor et al. | |
| 8,346,362 B2 | 1/2013 | Kinney et al. | |
| 8,391,983 B2 | 3/2013 | Lim | |
| 8,494,635 B2 | 7/2013 | Troetzschel et al. | |
| 8,528,201 B2 | 9/2013 | Troetzschel et al. | |
| 8,656,736 B2 | 2/2014 | Terao | |
| 8,742,268 B2 | 6/2014 | Reisinger et al. | |
| 2001/0013756 A1 | 8/2001 | Mori et al. | |
| 2004/0116976 A1 | 6/2004 | Spadgenske | |
| 2004/0128016 A1 | 7/2004 | Stewart | |
| 2006/0247714 A1 | 11/2006 | Taylor et al. | |
| 2006/0259093 A1 | 11/2006 | Stevenson et al. | |
| 2007/0183118 A1 | 8/2007 | Fu et al. | |
| 2008/0119906 A1 | 5/2008 | Starke | |
| 2008/0203917 A1 | 8/2008 | Maya | |
| 2008/0269831 A1 | 10/2008 | Erickson | |
| 2009/0192578 A1 | 7/2009 | Biggs | |
| 2009/0281586 A1 | 11/2009 | Lim | |
| 2010/0023086 A1 | 1/2010 | Lim | |
| 2010/0109966 A1 | 5/2010 | Mateychuk et al. | |
| 2010/0258342 A1 | 10/2010 | Parker | |
| 2011/0034965 A1 | 2/2011 | Troetzschel et al. | |
| 2011/0034966 A1 | 2/2011 | Troetzschel et al. | |
| 2011/0186349 A1 | 8/2011 | Troetzschel et al. | |
| 2012/0127627 A1 | 5/2012 | Brendel et al. | |
| 2012/0193117 A1 | 8/2012 | Specht et al. | |
| 2012/0193118 A1 | 8/2012 | Kempf et al. | |
| 2012/0193119 A1 | 8/2012 | Kempf et al. | |
| 2012/0193125 A1 | 8/2012 | Pavlovic et al. | |
| 2012/0193141 A1 | 8/2012 | Reisinger et al. | |
| 2012/0194981 A1 | 8/2012 | Kempf et al. | |
| 2012/0197326 A1 | 8/2012 | Pavlovic | |
| 2012/0197327 A1 | 8/2012 | Specht | |
| 2012/0197335 A1 | 8/2012 | Reisinger | |
| 2012/0197368 A1 | 8/2012 | Reisinger | |
| 2012/0200011 A1 | 8/2012 | Pavlovic | |
| 2012/0203294 A1 | 8/2012 | Troetzschel | |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 1685874 | 8/2006 |
| EP | 1754511 | 2/2007 |
| WO | 03073450 | 9/2003 |
| WO | 2004110555 | 12/2004 |
| WO | 2008103166 | 8/2008 |
| WO | 2010091435 | 8/2010 |

OTHER PUBLICATIONS

The Office Action for U.S. Appl. No. 13/361,340 mailed date Apr. 29, 2014 (18 pages).

The Office Action for U.S. Appl. No. 13/361,348 mailed date Feb. 19, 2014 (23 pages).

The Office Action for U.S. Appl. No. 13/361,362 mailed date Feb. 19, 2014 (19 pages).

The Office Action for U.S. Appl. No. 13/361,370 mailed date May 14, 2014 (18 pages).

The Office Action for U.S. Appl. No. 13/361,374 mailed date May 1, 2014 (20 pages).

The Notice of Allowance for U.S. Appl. No. 13/361,383 mailed date Apr. 25, 2014 (18 pages).

The Office Action for U.S. Appl. No. 13/361,388 mailed date Feb. 11, 2014 (24 pages).

The Office Action for U.S. Appl. No. 13/361,398 mailed date Mar. 7, 2014 (26 pages).

The Office Action for U.S. Appl. No. 13/361,404 mailed date Feb. 27, 2014 (19 pages).

The Restriction Requirement for U.S. Appl. No. 13/361,322 mailed Nov. 14, 2013 (7 pages).

The Office Action for U.S. Appl. No. 13/361,340 mailed Oct. 25, 2013 (20 pages).

The Restriction Requirement for U.S. Appl. No. 13/361,348 mailed Nov. 14, 2013 (7 pages).

The Office Action for U.S. Appl. No. 13/361,355 mailed Aug. 7, 2013 (21 pages).

The Restriction Requirement for U.S. Appl. No. 13/361,362 mailed Nov. 14, 2013 (7 pages).

The Office Action for U.S. Appl. No. 13/361,370 mailed Oct. 29, 2013 (26 pages).

The Restriction Requirement for U.S. Appl. No. 13/361,374 mailed Mar. 5, 2013 (6 pages).

The Office Action for U.S. Appl. No. 13/361,374 mailed Oct. 4, 2013 (22 pages).

The Restriction Requirement for U.S. Appl. No. 13/361,383 mailed Feb. 27, 2013 (6 pages).

The Office Action for U.S. Appl. No. 13/361,383 mailed Nov. 13, 2013 (22 pages).

The Restriction Requirement for U.S. Appl. No. 13/361,404 mailed Apr. 8, 2013 (6 pages).

The Restriction Requirement for U.S. Appl. No. 13/361,404 mailed Oct. 9, 2013 (5 pages).

The Notice of Allowance for U.S. Appl. No. 13/361,355 mailed Jan. 16, 2014 (18 pages).

* cited by examiner

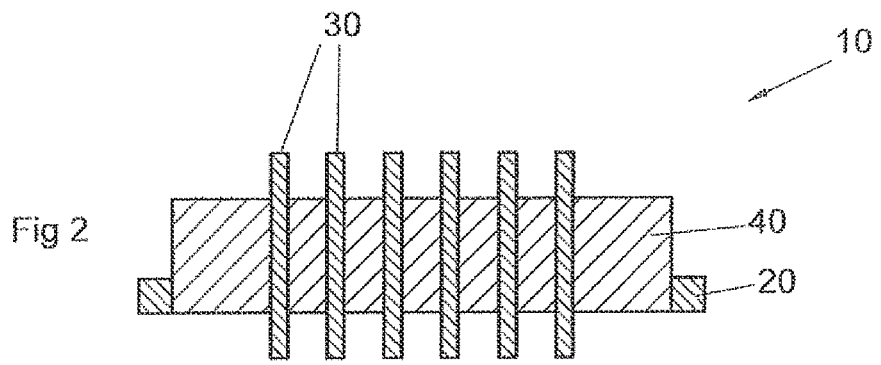
Fig 2
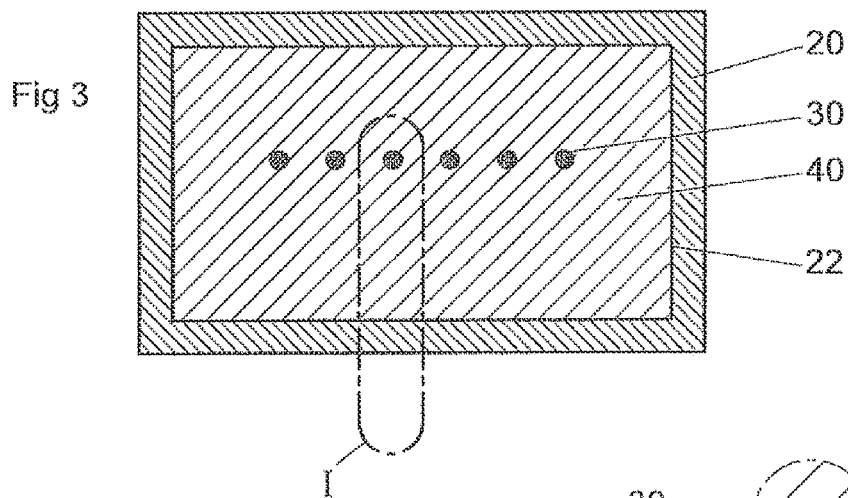
Fig 3
Fig 4
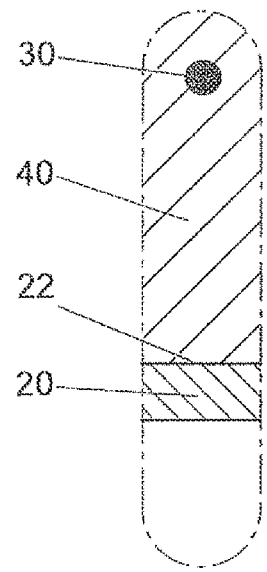

METHOD FOR MANUFACTURING AN ELECTRICAL BUSHING FOR AN IMPLANTABLE MEDICAL DEVICE

CROSS-REFERENCE TO RELATED APPLICATIONS

This Non-Provisional Patent Application claims the benefit of the filing date of U.S. Provisional Patent Application Ser. No. 61/438,063, filed Jan. 31, 2011, entitled "CERMET-CONTAINING BUSHING WITH HOLDING ELEMENT FOR AN IMPLANTABLE MEDICAL DEVICE," and this Patent Application also claims priority to German Patent Application No. DE 10 2011 009 862.3, filed on Jan. 31, 2011, and both of which are incorporated herein by reference.

This Patent Application is also related to patent application Ser. No. 13/361,322 filed on Jan. 30, 2012, entitled "CERAMIC BUSHING FOR AN IMPLANTABLE MEDICAL DEVICE"; patent application Ser. No. 13/361,340 filed on Jan. 30, 2012, entitled "DIRECTLY APPLICABLE ELECTRICAL BUSHING"; patent application Ser. No. 13/361,348 filed on Jan. 30, 2012, entitled "IMPLANTABLE DEVICE HAVING AN INTEGRATED CERAMIC BUSHING"; patent application Ser. No. 13/361,355 filed on Jan. 30, 2012, entitled "HEAD PART FOR AN IMPLANTABLE MEDICAL DEVICE"; patent application Ser. No. 13/361,362 filed on Jan. 30, 2012, entitled "CERMET-CONTAINING BUSHING FOR AN IMPLANTABLE MEDICAL DEVICE HAVING A CONNECTING LAYER"; patent application Ser. No. 13/361,370 filed on Jan. 30, 2012, entitled "ELECTRICAL BUSHING WITH CERMET-CONTAINING CONNECTING ELEMENT FOR AN ACTIVE IMPLANTABLE MEDICAL DEVICE"; patent application Ser. No. 13/361,374 filed on Jan. 30, 2012, entitled "CERAMIC BUSHING WITH FILTER"; patent application Ser. No. 13/361,383 filed on Jan. 30, 2012, entitled "CERAMIC BUSHING WITH INDUCTIVE FILTER"; patent application Ser. No. 13/361,388 filed on Jan. 30, 2012, entitled "CERAMIC BUSHING HAVING HIGH CONDUCTIVITY CONDUCTING ELEMENTS"; patent application Ser. No. 13/361,398 filed on Jan. 30, 2012, entitled "METHOD FOR THE MANUFACTURE OF A CERMET-CONTAINING BUSHING"; and patent application Ser. No. 13/361,404 filed on Jan. 30, 2012, entitled "METHOD FOR THE MANUFACTURE OF A CERMET-CONTAINING BUSHING FOR AN IMPLANTABLE MEDICAL DEVICE".

BACKGROUND

One aspect relates to an electrical bushing for use in a housing of an implantable medical device. Moreover, one aspect relates to a method for the manufacture of an electrical bushing for an implantable medical device.

The post-published document, DE 10 2009 035 972, discloses an electrical bushing for an implantable medical device having the features of the preamble of claim 1. Moreover, a use of at least one cermet-comprising conducting element in an electrical bushing for implantable medical device and a method for the manufacture of an electrical bushing for an implantable medical device are disclosed.

A multitude of electrical bushings for various applications are known, examples including: U.S. Pat. Nos. 4,678,868, 7,564,674 B2, US 2008/0119906 A1, U.S. Pat. Nos. 7,145,076 B2, 7,561,917, US 2007/0183118 A1, U.S. Pat. Nos. 7,260,434B1, 7,761,165, U.S. Pat. Nos. 7,742,817 B2, 7,736,191 B1, US 2006/0259093 A1, U.S. Pat. No. 7,274,963 B2, US 2004116976 A1, U.S. Pat. No. 7,794,256, US 2010/0023086 A1, U.S. Pat. Nos. 7,502,217 B2, 7,706,124 B2, 6,999,818 B2, EP 1754511 A2, U.S. Pat. No. 7,035,076, EP 1685874 A1, WO 03/073450 A1, U.S. Pat. Nos. 7,136,273, 7,765,005, WO 2008/103166 A1, US 2008/0269831, U.S. Pat. No. 7,174,219 B2, WO 2004/110555 A1, U.S. Pat. No. 7,720,538 B2, WO 2010/091435, US 2010/0258342 A1, US 2001/0013756 A1, U.S. Pat. No. 4,315,054, and EP 0877400.

DE 697 297 19 T2 describes an electrical bushing for an active implantable medical device—also called implantable device or therapeutic device. Electrical bushings of this type serve to establish electrical connection between a hermetically sealed interior and an exterior of the therapeutic device. Known implantable therapeutic devices are cardiac pacemakers or defibrillators, which usually include a hermetically sealed metal housing which is provided with a connection body, also called header, on one side. Said connection body includes a hollow space having at least one connection socket that serves for connecting electrode leads. In this context, the connection socket includes electrical contacts in order to electrically connect electrode leads to the control electronics on the interior of the housing of the implantable therapeutic device. Hermetic sealing with respect to a surrounding is an essential prerequisite of an electrical bushing of this type. Therefore, lead wires that are introduced into an electrically insulating base body—also called signal-transmission elements—through which the electrical signals are propagated, must be introduced into the base body such as to be free of gaps. In this context, it has proven to be challenging that the lead wires generally are made of a metal and are introduced into a ceramic base body. In order to ensure durable connection between the two elements, the internal surface of a through-opening—also called openings—in the base body is metallized in order to attach the lead wires by soldering. However, the metallization has proven to be difficult to apply in the through-opening. Only cost-intensive procedures ensure homogeneous metallization of the internal surface of the bore hole—and thus a hermetically sealed connection of the lead wires to the base body by soldering. The soldering process itself requires additional components, such as solder rings. Moreover, the process of connecting the lead wires to the previously metallized insulators utilizing the solder rings is a process that is laborious and difficult to automate.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally corresponding elements are identified through the same reference numbers. The invention shall not be limited to the exemplary embodiments.

FIG. 2 illustrates a sectional drawing through an electrical bushing according to one embodiment.

FIG. 3 illustrates a schematic top view onto the electrical bushing according to FIG. 2.

FIG. 4 illustrates a magnified detail of the electrical bushing.

DETAILED DESCRIPTION

Figure 1:
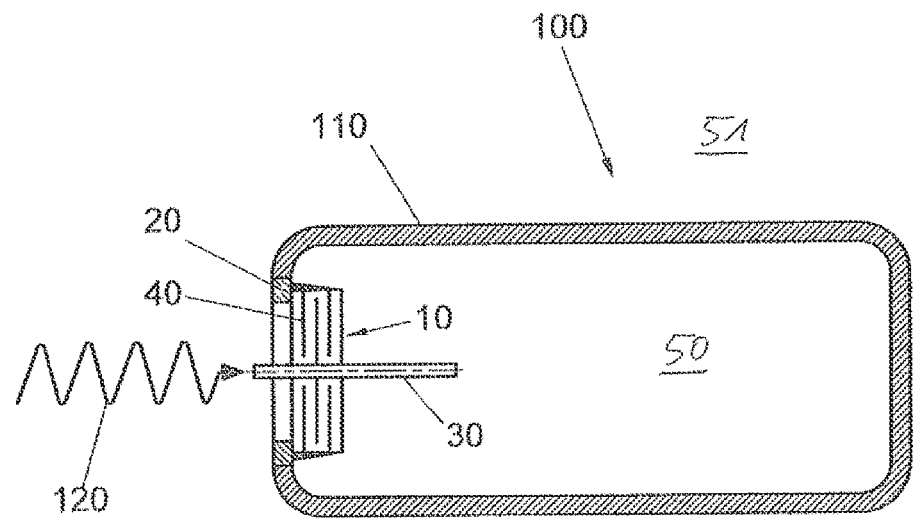
FIG. 1 illustrates an implantable medical device.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment creates an electrical bushing for an implantable medical device, in which at least one of the disadvantages mentioned above is prevented at least in part. One embodiment creates a durable connection of an electrical bushing in or on a housing of a medical device. Features and details that are described in the context of the electrical bushing or the implantable medical device shall also apply in relation to the method, and vice versa.

In summary, the following embodiments are proposed:

An electrical bushing for use in a housing of an implantable medical device, whereby the electrical bushing includes at least one electrically insulating base body and at least one electrical conducting element, whereby the electrical bushing further includes at least one holding element in order to hold the electrical bushing in or on a housing, whereby the conducting element is set-up to establish, through the base body, at least one electrically conducting connection between an internal space of the housing and an external space, whereby the conducting element is hermetically sealed with respect to the base body, whereby the at least one conducting element includes at least one cermet, whereby the holding element in one embodiment consists of at least 80% by weight, in one embodiment at least 90% by weight, and in one embodiment at least 99% by weight, each with respect to the holding element (20), of a material selected from the group consisting of a metal from any of subgroups V, VI, VIII, IX and X of the periodic system of the elements or at least two of these. The selection of suitable materials includes all substances and mixtures thereof that are known to a person skilled in the art and are characterized, for example, by high bio-compatibility. Consequently, said materials are to withstand the conditions inside the body, in which the medical device having the electrical bushing according to one embodiment is inserted, for as long as possible and essentially without being changed. Metals, mixtures and alloys from the above-mentioned subgroups, for example, are possibilities in this regard. The mixtures and alloys can involve either the metals of the above-mentioned subgroups or mixtures and alloys made from one or more of these metals and other metals can be used. Mainly, those mixtures and alloys that are capable of forming a stable connection to the base body of the electrical bushing are preferred in one embodiment.

In one embodiment, the material is selected from the group consisting of platinum (Pt), iron (Fe), iridium (Ir), niobium (Nb), molybdenum (Mo), tungsten (W), titanium (Ti), cobalt (Co), chromium (Cr), for example, cobalt-chromium alloys, and zirconium (Zr) as well as at least two of these, with Ti, Nb, Mo, Co, Cr and alloys thereof being. Said metals can each be used alone or in combination with each other or in combination with other materials, such as other metals. For example, alloys made of niobium and one of the other above-mentioned metals are preferred in one embodiment. Iron alloys, often referred to as stainless steel, are also preferred in one embodiment. Platinum and platinum alloys as well as cobalt-chromium alloys are also preferred in one embodiment.

In an embodiment of the electrical bushing according to one embodiment, the base body and the at least one conducting element are connected in a firmly bonded manner, for example, through a firmly bonded sintered connection. The process of sintering shall be illustrated in more detail below.

In an embodiment of the electrical bushing according to one embodiment, the base body is made, at least in part, from an insulating composition of materials.

In an embodiment of the electrical bushing, the insulating composition of materials is selected from the group consisting of: aluminum oxide, magnesium oxide, zirconium oxide, aluminum titanate and piezoceramic materials. Processed into ceramic materials, said materials display particularly high thermal resistance, mechanical strength, and inert behavior with respect to acids and bases. This renders them particularly well-suited for use as a biocompatible material in implantable medical devices.

The proposed electrical bushing is set-up for use in an implantable medical device, whereby the implantable medical device can be provided, in one embodiment, as an active implantable medical device (AIMD) and in one embodiment as a therapeutic device.

As a matter of principle, the term, implantable medical device, shall include any device which is set-up to perform at least one medical function and which can be introduced into a body tissue of a human or animal user. As a matter of principle, the medical function can include any function selected from the group consisting of a therapeutic function, a diagnostic function, and a surgical function. For example, the medical function can include at least one actuator function, in which an actuator is used to exert at least one stimulus on said body tissue, for example, an electrical stimulus.

As a matter of principle, the term, active implantable medical device—also called AIMD—shall include all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The implantable medical device, for example, the active implantable medical device, can usually include, for example, at least one housing, for example, at least one hermetically sealed housing. The housing can in one embodiment enclose at least one electronics unit, for example a triggering and/or analytical electronics unit of the implantable medical device.

In the scope of one embodiment, a housing of an implantable medical device shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element with respect to strains occurring during operation and/or upon handling, and/or protection to the functional element with respect to influences from its surroundings such as, for example, influences of a body fluid. The housing can, for example, border and/or close the implantable medical device with respect to the outside.

In this context, an internal space shall be understood herein to mean a region of the implantable medical device, for example, within the housing, which can take up the functional element fully or in part and which, in an implanted state, does not contact the body tissue and/or a body fluid. The internal space can include at least one hollow space which can be closed fully or in part. Alternatively, the internal space can be filled fully or in part, for example, by the at least one functional element and/or by at least one filling material, for example at least one casting, for example at least one casting material in the form of an epoxy resin or a similar material.

An external space, in contrast, shall be understood to be a region outside of the housing. This can, for example, be a region which, in the implanted state, can contact the body tissue and/or a body fluid. Alternatively or in addition, the external space can just as well be or include a region that is only accessible from outside the housing without necessarily contacting the body tissue and/or the body fluid, for example a region of a connecting element of the implantable medical device that is accessible from outside to an electrical connecting element, for example an electrical plug connector.

The housing and/or, for example, the electrical bushing can, for example, be provided to be hermetically sealed such that, for example, the internal space, is hermetically sealed with respect to the external space. In this context, the term, "hermetically sealed", can illustrate that moisture and/or gases cannot permeate through the hermetically sealed element at all or only to a minimal extent upon intended use for the common periods of time (for example 5-10 years). The leakage rate, which can be determined, for example, by leak tests, is a physical parameter that can described, for example, a permeation of gases and/or moisture through a device, for example, through the electrical bushing and/or the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of one embodiment, said maximal permissible helium leak rates can, for example, be from $1\times10^{-8}$ atm*cm$^3$/sec to $1\times10^{-7}$ atm*cm$^3$/sec. In the scope of one embodiment, the term, "hermetically sealed", shall be understood, for example, to mean that the device to be tested (for example the housing and/or the electrical bushing and/or the housing with the electrical bushing) has a helium leak rate of less than $1\times10^{-7}$ atm*cm$^3$/sec. In one embodiment, the helium leak rate can be less than $1\times10^{-8}$ atm*cm$^3$/sec, in one embodiment, less than $1\times10^{-9}$ atm*cm$^3$/sec. For the purpose of standardization, the above-mentioned helium leak rates can also be converted into the equivalent standard air leak rate. The definition of the equivalent standard air leak rate and the conversion are specified in the ISO 3530 standard.

Electrical bushings are elements set-up to create at least one electrically conducting path that extends between the internal space of the housing to at least one external point or region outside the housing, for example, situated in the external space. Accordingly, this establishes an electrical connection to leads, electrodes, and sensors that are arranged outside the housing, for example.

Common implantable medical devices are commonly provided with a housing, which can include, on one side, a head part, also called header or connecting body, that carries connection sockets for connection of leads, also called electrode leads. The connection sockets include, for example, electrical contacts that serve to electrically connect the leads to a control electronics unit on the interior of the housing of the medical device. Usually, an electrical bushing is provided in the location, at which the electrical connection enters into the housing of the medical device, and the electrical bushing is inserted into a corresponding opening of the housing in a hermetically sealing manner.

Due to the type of use of implantable medical devices, their hermetic sealing and biocompatibility are usually amongst the foremost requirements. The implantable medical device proposed herein according to one embodiment, can be inserted, for example, into a body of a human or animal user, for example, of a patient. As a result, the implantable medical device is usually exposed to a fluid of a body tissue of the body. Accordingly, it is usually important that no body fluid penetrates into the implantable medical device and that no liquids leak from the implantable medical device. In order to ensure this, the housing of the implantable medical device, and thus the electrical bushing as well, should be as impermeable as possible, for example, with respect to body fluids.

Moreover, the electrical bushing should ensure high electrical insulation between the at least one conducting element and the housing and/or the multiple conducting elements provided that more than one conducting element are present. In this context, in one embodiment the insulation resistance reached is at least several MOhm, in one embodiment, more than 20 MOhm, and the leakage currents reached can be small, in one embodiment, less than 10 pA. Moreover, in case multiple conducting elements are present, the crosstalk and electromagnetic coupling between the individual conducting elements in one embodiment are below the specified thresholds for medical applications.

The electrical bushing disclosed according to one embodiment is particularly well-suited for the above-mentioned applications. Moreover, the electrical bushing can also be used in other applications that are associated with special requirements with regard to biocompatibility, tight sealing, and stability.

The electrical bushing according to one embodiment can meet, for example, the above-mentioned tight sealing requirements and/or the above-mentioned insulation requirements.

As mentioned above, the electrical bushing includes at least one electrically insulating base body. In the scope of one embodiment, a base body shall be understood to mean an element that serves a mechanical holding function in the electrical bushing, for example in that the base body holds or carries the at least one conducting element either directly or indirectly. For example, the at least one conducting element can be embedded in the base body directly or indirectly, fully or partly, for example, through a firmly bonded connection between the base body and the conducting element and for example, through co-sintering the base body and the conducting element. For example, the base body can have at least one side facing the internal space and at least one side facing the external space and/or accessible from the external space.

As mentioned above, the base body is provided to be electrically insulating. This means that the base body, fully or at least regions thereof, is made of at least one electrically insulating material. In this context, an electrically insulating material shall be understood to mean a material with a resistivity of at least $10^7$ Ohm*m, in one embodiment, of at least $10^8$ Ohm*m, in one embodiment of at least $10^9$ Ohm*m, and in one embodiment of at least $10^{11}$ Ohm*m. For example, the base body can be provided such that, as mentioned above, a flow of current between the conducting element and the housing and/or between multiple conducting elements is at least largely prevented, for example through the resistivity values between the conducting element and the housing as specified above being implemented. For example, the base body can include at least one ceramic material.

In this context, a conducting element or electrical conducting element shall generally be understood to mean an element set-up to establish an electrical connection between at least two sites and/or at least two elements. For example, the conducting element can include one or more electrical conductors, for example metallic conductors. In the scope of one embodiment, the conducting element is made fully or partly of at least one cermet, as mentioned above. In addition, one or more other electrical conductors, for example metallic conductors, can be provided. The conducting element can, for example, be provided in the form of one or more contact pins and/or curved conductors. Moreover, the conducting element can include, for example, on a side of the base body and/or electrical bushing facing the internal space or on a side of the base body and/or electrical bushing facing the external space or accessible from the external space, one or more connecting contacts, for example one or more plug-in connectors, for example one or more connecting contacts, which project from the base body or can be electrically contacted through other means from the internal space and/or the external space.

The at least one conducting element can establish the electrically conducting connection between the internal space and the external space in a variety of ways. For example, the conducting element can extend from at least one section of the conducting element that is arranged on the side of the base body facing the internal space to at least one section of the conducting element arranged on the side facing the external space or accessible from the external space. However, other arrangements are also feasible as a matter of principle. Accordingly, the conducting element can just as well include a plurality of partial conducting elements that are connected to each other in an electrically conducting manner. Moreover, the conducting element can extend into the internal space and/or the external space. For example, the conducting element can include at least one region that is arranged in the internal space and/or at least one region that is arranged in the external space, whereby the regions can, for example, be electrically connected to each other. Various exemplary embodiments shall be illustrated in more detail below.

The at least one conducting element can include, on a side of the base body and/or electrical bushing facing the internal space or on a side of the base body and/or electrical bushing facing the external space or accessible from the external space, at least one electrical connecting element and/or be connected to an electrical connecting element of this type. For example, as described above, one or more plug-in connectors and/or one or more contact surfaces and/or one or more contact springs and/or one or more types of electrical connecting elements can be provided on one or both of said sides. The at least one optional connecting element can, for example, be a component of the at least one conducting element and/or can be connected to the at least one conducting element in an electrically conducting manner. For example, one or more conducting elements of the bushing can be contacted to one or more internal connecting elements and/or one or more external connecting elements. The material of the internal connecting elements should be suited for permanent connection to the conducting element. The external connecting elements should be biocompatible and should be such that they can be permanently connected to the at least one conducting element.

The electrically insulating base body can support, as a bearing, for example, the at least one conducting element. The at least one material of the base body should be biocompatible in one embodiment, as mentioned above, and should have sufficiently high insulation resistance. It has proven to be advantageous in one embodiment for the base body to include one or more materials selected from the group consisting of: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate.

The holding element includes the base body and serves as connecting element to the housing of the implantable device. The materials of the holding element should be biocompatible, easy to process, corrosion-resistant, and permanently connectable to the base body and the housing in a firmly bonded manner. It has proven to be advantageous for the holding element according to one embodiment to include at least one of the following metals and/or an alloy based on at least one of the following metals: platinum, iridium, niobium, molybdenum, tantalum, tungsten, titanium, cobalt-chromium alloys or zirconium.

In the proposed electrical bushing, the at least one conducting element includes at least one cermet.

The base body can, for example, be made fully or partly from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors.

In the scope of one embodiment, "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added.

In the scope of one embodiment, sintering or a sintering process shall generally be understood to mean a method for producing materials or work-pieces, in which powdered, for example, fine-grained, ceramic and/or metallic substances are heated and thus connected. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, in one embodiment, at least 100 bar, or even at least 1000 bar. The process can proceed, for example, fully, or partly at temperatures below the melting temperature of the powdered materials, for example at temperatures of 700° C. to 1400° C. The process can be implemented, for example, fully, or partly in a tool and/or a mold such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

Producing the at least one conducting element and/or optionally producing the at least one base body, a method can be used for example, in which at least one green compact is produced first, subsequently at least one brown compact is produced from said green compact, and subsequently the finished work-piece is produced from said brown compact through at least one sintering step. In this context, separate green compacts and/or separate brown compacts can be produced for the conducting element and the base body and can be connected subsequently. Alternatively, one or more common green compacts and/or brown compacts can be produced for the base body and the conducting element. Alternatively again, separate green compacts can be produced first, said green compacts can then be connected, and subsequently a common brown compact can be produced from the connected green compact. In general, a green compact shall be understood to mean a pre-form body of a work-piece which includes the starting material, for example the at least one ceramic and/or metallic powder, as well as, if applicable, the one or more binding agents and/or one or more solvents. A brown compact shall be understood to mean a pre-form body which is generated from the green compact through at least one debinding step, for example at least one thermal and/or chemical debinding step, whereby the at least one binding agent and/or the at least one solvent is removed, at least partly, from the pre-form body in the debinding step.

The sintering process, for example, of a cermet, but of the base body just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the bushing according to one embodiment, the at least one ceramic component of the cermet can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, or sodium-potassium-niobate.

For the bushing according to one embodiment, the at least one metallic component of the cermet can include, for example, at least one of the following metals and/or an alloy based on at least one of the following metals: platinum, iridium, niobium, molybdenum, tantalum, tungsten, titanium, cobalt or zirconium. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that the metal content should be 25% by volume and more, in one embodiment 32% by volume, in one embodiment, more than 38% by volume, depending on the selection of materials.

In the scope of one embodiment, the terms, "including a cermet," "cermet-including," "comprising a cermet," and "cermet-containing", are used synonymously. Accordingly, the terms refer to the property of an element, being that the element contains cermet. This meaning also includes the variant of an embodiment in that elements, for example the conducting element, consist of a cermet, that is, are fully made of a cermet.

In one embodiment, both the at least one conducting element and the base body can include one or more components which are or can be produced in a sintering procedure, or the at least one conducting element and the base body are or can both be produced in a sintering procedure. For example, the base body and the conducting element are or can be produced in a co-sintering procedure, that is, a procedure of simultaneous sintering of these elements. For example, the conducting element and the base body each can include one or more ceramic components that are produced, and in one embodiment compacted, in the scope of at least one sintering procedure.

For example, a base body green compact can be produced from an insulating composition of materials. This can proceed, for example, by compressing the composition of materials in a mold. In this context, the insulating composition of materials in one embodiment is a powder mass, in which the powder particles illustrate at least minimal cohesion. In this context, the production of a green compact proceeds, for example, through compressing powder masses or through forming followed by drying.

Said procedural steps can also be utilized to form at least one cermet-containing conducting element green compact. In this context, one embodiment can provide that the powder, which is compressed into the conducting element green compact, is cermet-containing or consists of a cermet or includes at least one starting material for a cermet. Subsequently, the two green compacts—the base body green compact and the conducting element green compact—can be combined. The production of the conducting element green compact and the base body green compact can just as well proceed simultaneously, for example, by multi-component injection molding, co-extrusion, etc., such that there is no longer a need to connect them subsequently.

While the green compacts are being sintered, they are in one embodiment subjected to a heat treatment below the melting temperature of the powder particles of the green compact. This usually leads to compaction of the material and ensuing substantial reduction of the porosity and volume of the green compacts. Accordingly, in one embodiment of the method the base body and the conducting element can be sintered jointly. Accordingly, there is in one embodiment no longer a need to connect the two elements subsequently.

Through the sintering, the conducting element becomes connected to the base body in one embodiment in a positive fit-type and/or non-positive fit-type and/or firmly bonded manner. In one embodiment, this achieves hermetic integration of the conducting element into the base body. In one embodiment, there is no longer a need for subsequent soldering or welding of the conducting element into the base body. Rather, a hermetically sealing connection between the base body and the conducting element is attained through the joint sintering in one embodiment and utilization of a cermet-containing green compact in one embodiment.

One refinement of the method is characterized in that the sintering includes only partial sintering of the at least one optional base body green compact, whereby said partial sintering can effect and/or include, for example, the debinding step mentioned above. The green compact is in one embodiment heat-treated in the scope of said partial sintering. This is usually already associated with some shrinkage of the volume of the green compact. However, the volume of the green compact has not yet reached its final state. Rather, another heat treatment is usually needed—a final sintering—in which the green compact(s) is/are shrunk to their final size. In the scope of said variant of an embodiment, the green compact is in one embodiment sintered only partly in order to attain some stability to render the green compact easier to handle.

The starting material used for producing at least one conducting element green compact and/or at least one base body green compact can, for example, be a dry powder or include a dry powder, whereby the dry powder is compressed in the dry state into a green compact and illustrates sufficient adhesion to maintain its compressed green compact shape. However, optionally, the starting material can include one or more further components in addition to the at least one powder, for example, as mentioned above, one or more binding agents and/or one or more solvents. Said binding agents and/or solvents, for example organic and/or inorganic binding agents and/or solvents, are generally known to the person skilled in the art, and are commercially available. The starting material can, for example, include one or more slurries or be a slurry. In the scope of one embodiment, a slurry is a suspension of particles of a powder made of one or more materials in a liquid binding agent, and, if applicable, in a water-based or organic binding agent. A slurry has a high viscosity and can easily be shaped into a green compact without the application of high pressure.

In the case of green compacts made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads to a rapid increase of the volume of the binding agent by transition to the gas phase and destruction of the green compact or formation of undesired defects in the work-piece.

Thermoplastic and duroplastic polymers, waxes, thermogelling substances and/or surface-active substances, for example, can be used as binding agent—also called binder. In this context, these can be used alone or as binding agent mixtures of multiple components of this type. If individual elements or all elements of the bushing (base body green compact, conducting element green compact, bushing blank) are produced in the scope of an extrusion procedure, the composition of the binding agent should be such that the line of the elements extruded through the nozzle is sufficiently stable in shape for the shape defined by the nozzle to easily be maintained. Suitable binders, also called binding agents, are known to the person skilled in the art.

In contrast, the conducting element according to the prior art usually is a metal wire. A conducting element provided with a cermet, as is in accordance with one embodiment, can be connected easily to the base body since it is a ceramic material. Accordingly, green compacts of both the conducting element and the base body can be produced and subsequently subjected to a sintering process. The resulting electrical bushing is not only biocompatible and durable, but also possesses good hermetic sealing properties. Thus, no fissures or connecting sites still to be soldered result between the conducting element and the base body. Rather, sintering results in the base body and the conducting element becoming connected. A variant of an embodiment therefore provides the at least one conducting element to consist of a cermet. In this variant of an embodiment, the conducting element includes not only components made of cermet, but is fully made of a cermet.

Generally, cermets are characterized by their particularly high toughness and wear resistance. The "cermets" and/or "cermet-containing" substances can, for example, be or include cutting materials related to hard metals which can dispense with tungsten carbide as the hard substance and can be produced, for example, by a powder metallurgical route. A sintering process for cermets and/or the cermet-containing conducting element proceeds, for example, alike a process for homogeneous powders except that, at identical compression force, the metal is usually compacted more strongly than the ceramic material. Compared to sintered hard metals, the cermet-containing conducting element usually illustrates higher resistance to thermal shock and oxidation.

As mentioned above, the ceramic components, for example, in the base body, can be, in one embodiment, aluminum oxide ($Al_2O_3$) and/or zirconium dioxide ($ZrO_2$), whereas in one embodiment, niobium, molybdenum, titanium, cobalt, zirconium, chromium are conceivable as metallic components, which are in one embodiment used in the holding element. In one embodiment, the ceramic component, $Al_2O_3$, in combination with niobium, iron, platinum or molybdenum is preferred. The ceramic component, $ZrO_2$, combined with niobium as metallic component is an alternative. The preceding combinations are particularly well-suited for the connecting according to one embodiment, which is often referred to as "diffusion-bonding".

For integration of the electrical bushing in the housing of a cardiac pacemaker, the electrical bushing includes a holding element. In one embodiment, said holding element is arranged to be situated around an entire surface of the base body. Depending on the shape of the base body, the holding element is arranged around the base body, for example, in an annular or ring shape. The purpose of the holding element is to establish a non-positive fit- and/or positive fit-type connection of the base body to the housing. A hermetically sealed connection between the holding element and the housing is to be formed in the process. In one embodiment, the holding element includes a composition of materials, in which the metal oxide fraction, such as of aluminum oxide ($Al_2O_3$), magnesium oxide ($MgO$), zirconium oxide ($ZrO_2$), aluminum titanate ($Al_2TiO_5$), and piezoceramic materials, is less than 20% by weight with respect to the holding element. In one embodiment, the fraction of metal oxides is less than 10% by weight and in one embodiment is less than 1% by weight, each with respect to the holding element. In one embodiment, the electrical bushing includes a holding element that does not include a cermet. The effect of the low metal oxide fraction is that the holding element is not only easy to manufacture and to connect to the electrical bushing, but also is more flexible in use than a holding element with a metal oxide fraction that is too high. The higher the metal oxide fraction, the less deformable is the holding element, which can lead to the handling of the holding element becoming more inflexible. Moreover, the holding element is particularly flexible in use if it can also be connected easily to other materials, such as, for example, a housing of a device. This is more likely to be provided by the holding element having a high metal content, as proposed according to one embodiment, than with a cermet or a ceramic material.

The metal-containing holding element can be connected to the housing of the implantable medical device in an easy, durable and hermetically sealed manner. Since both the holding element and the conducting element are still to be connected to metallic components, both should include means to be welded or soldered to them. In an embodiment according to one embodiment, the holding element consists, at least in part, of a material selected from the group consisting of platinum (Pt), iron (Fe), iridium (Ir), niobium (Nb), molybdenum (Mo), tungsten (W), titanium (Ti), cobalt (Co), chromium (Cr), for example, cobalt-chromium alloys, and zirconium (Zr) as well as at least two of these or alloys that include other metals.

One embodiment includes a base body that is formed from an insulating composition of materials. The purpose of the base body is to insulate the conducting wire from the holding element and the other objects of the implantable medical device. Electrical signals that are propagated through the conducting wire shall not be attenuated or short-circuited by contacting the housing of the implantable device. In addition, the composition of the base body must be biocompatible for implantation in medical applications. For this reason, it is preferred in one embodiment that the base body consists of a glass-ceramic or glass-like material. It has been found to be preferred in one embodiment that the insulating composition of materials of the base body is at least any one from the group, aluminum oxide ($Al_2O_3$), magnesium oxide (MgO), zirconium oxide ($ZrO_2$), aluminum titanate ($Al_2TiO_5$), and piezoceramic materials. In this context, aluminum oxide features high electrical resistance and low dielectric losses. These properties are supplemented by the additional high thermal resistance and good biocompatibility.

Another refinement of the bushing according to one embodiment is characterized in that the holding element includes at least one flange, whereby the flange, for example, is electrically conductive. The purpose of the flange is to seal the electrical bushing with respect to a housing of the implantable device. The holding element holds the electrical bushing in the implantable device. In the variant of an embodiment described herein, the holding element includes at least one flange on an external side. These flanges form a bearing, which can be engaged by the lids of the implantable medical device, for example, engaged in a tightly sealing manner. Accordingly, the holding element including the flanges connected to it can have a U- or H-shaped cross-section. Integrating at least one flange into the holding element ensures that the electrical bushing is integrated into the implantable device in a safe, impact-resistant and durable manner.

The scope of one embodiment also includes an implantable medical device, for example, a cardiac pacemaker or defibrillator, having an electrical bushing according to at least one of the preceding claims. Features and details that were described in the context of the electrical bushing and/or the method shall obviously also apply in relation to the implantable medical device.

Moreover, one embodiment also relates to a method for the manufacture of an electrical bushing for an implantable medical device.

According to another aspect of one embodiment, a method for the manufacture of an electrical bushing for an implantable medical device is proposed, whereby the method includes the following steps:

a) generating at least one base body green compact for at least one base body from an insulating composition of materials;

b) forming at least one cermet-containing conducting element green compact for at least one conducting element;

c) introducing the at least one conducting element green compact into the base body green compact;

d) connecting the base body green compact to the at least one conducting element green compact in order to obtain at least one base body having at least one conducting element;

whereby the base body is connected to a holding element at a temperature between 100° C. and 3,000° C.

The base body can be connected to the holding element, for example, by simply contacting the two elements at the elevated temperature by heating the two bodies for several minutes, for example 10 to 1000, or hours, in one embodiment 0.2 to 50, in one embodiment 0.5 to 3, to a higher temperature than room temperature. The temperature selection depends mainly on the selection of materials for the base body and the holding element. Accordingly, it is customary to select for a connecting process of this type, also called "diffusion bonding", a temperature that corresponds to approx. 50-90% of the temperature of the higher melting material. This can be between 100° C. and 3,000° C., in one embodiment between 500° C. and 2,700° C., in one embodiment between 700° C. and 2,500° C., for the materials according to one embodiment. It is customary to select the temperatures such that these are below the lowest melting material that is included in the method according to one embodiment.

Usually, "diffusion bonding", shall be understood to mean a process, in which two bodies made of different materials which are otherwise difficult to connect are made to form a stable connection. For this purpose, two different materials are contacted with each other at suitable temperature and pressure conditions and kept at these conditions for a certain period of time. At these temperatures and pressures acting on the connecting surfaces of the two materials, which are usually elevated as compared to standard conditions, some mass transport proceeds between the two bodies that can establish a very stable connection between the two bodies.

The principle of "diffusion bonding" and the properties of the resulting links between two different materials are described in the publication by Shizadi A. A. in Journal of Surface and Interface Analysis, vol. 31, no. 7 on pages 609-618, such that reference shall be made herewith to the implementation of said process and the properties of the materials thus processed.

In a further refinement according to one embodiment, the pressure acting on the base body and the holding element while the holding element is being connected to the base body is 0.2 to 20 MPa, in one embodiment in a range from 1 to 12 MPa. The pressure can be applied, for example, by means of a weight that is placed on the base body or the holding element. Moreover, it is preferred in one embodiment that the pressure, in one embodiment a starting pressure, during the connecting process is less than $1*10^{-4}$ mbar. Usually, the connecting process is carried out in a vacuum furnace.

In another refinement according to one embodiment, the holding element consists of a metal, at least in part. In one embodiment, the holding element is made from a material selected from the group consisting of a metal from any of the subgroups IV, V, VI, VIII, IX, and X of the periodic system of the elements or at least two thereof. Moreover, in an embodiment according to one embodiment, the metal is selected from the group consisting of platinum, iridium, niobium, iron, molybdenum, tantalum, tungsten, titanium, cobalt, chromium, in one embodiment, cobalt-chromium alloys, and zirconium or two thereof.

Said metals can each be used alone or in combination with another material. Said other material can be the above-mentioned metals and alloys or further materials such as further metals. Alternatively or in addition, alloys made from several of the above-mentioned metals can be used. Alternatively or in addition, mixtures or alloys made from one or more of the above-mentioned metals and one or more further metals can be used just as well. These can be, for example, mixtures including non-metals such as metal oxides, such as ZrO, $ZrO_2$, $Al_2O_3$ and other ceramic materials.

In an embodiment according to one embodiment, the holding element includes niobium and the base body includes a zirconium oxide. The zirconium oxide can be a zirconium(II) oxide (ZrO) or a zirconium(IV) oxide ($ZrO_2$) or a mixture thereof. In one embodiment, the base body includes a zirconium(IV) oxide. Zirconium(IV) oxide is particularly resistant to the action of acids and alkaline solutions which renders it particularly well-suited for use in a medical device that may contact both body fluids of various pH values and liquids and/or vapors and substances inside the device that also may be alkaline or acidic. Moreover, as a fired powder, $ZrO_2$ forms a particularly hard and resistant ceramic substance. The combination of $ZrO_2$ for the base body and niobium for the holding element has proven to be particularly stable when exposed to mechanical strain. The combination of $ZrO_2$-comprising base body and Nb-containing holding element allows a good connection by "diffusion bonding" to be attained.

In a refinement of the method according to one embodiment, the holding element includes a material selected from the group consisting of niobium (Nb), platinum (Pt), iron (Fe), and molybdenum (Mo) or at least two of these, and the base body includes an aluminum oxide. As a ceramic material, aluminum oxide ($Al_2O_3$) features high mechanical resistance and is very well-suited for binding to metals such as Nb, Pt, Fe, Mo by "diffusion bonding". In turn, said metals can be attached well to other components, such as, for example, a housing of a medical device, by welding, soldering or bonding.

It is preferable in one embodiment for the base body green compact to be subjected to firing together with the at least one conducting element green compact.

In a refinement of the method, the base body green compact is subjected to firing together with the at least one base body green compact. Said process can, for example, be a sintering. Sintering can be used in one embodiment for powder-like substances. This results in particularly tough, inert, and stable bodies being obtained, which, in addition, are biocompatible in the majority of cases. Said bodies are particularly suitable for use in implantable devices.

In another refinement according to one embodiment, step a) of the preceding method described above includes a partial sintering of the base body green compact.

In another refinement according to one embodiment, step b) of the preceding method described above includes a partial sintering of the conducting element green compact.

Moreover, an electrical bushing is proposed that can be obtained having the method features of the embodiments of the method described above.

The scope of one embodiment also includes an implantable medical device, for example, cardiac pacemaker or defibrillator, having at least one electrical bushing according to at least one of the preceding embodiments.

The scope of one embodiment also includes the use of an electrical bushing according to any one of the embodiments of the electrical bushing for an implantable medical device described above.

The special feature of the method according to one embodiment results from both the base body and the conducting element comprising ceramic components that can be processed in the scope of a sintering process. In the scope of step a), a base body green compact is generated from an insulating composition of materials. This can be done by compressing the composition of materials in a mold. In this context, the insulating composition of materials in one embodiment is a powder mass, in which the powder particles illustrate at least minimal cohesion. Usually, this is effected in that a grain size of the powder particles does not exceed 0.5 mm. In this context, the manufacture of the green compact proceeds either by compressing powder masses or by forming and subsequent drying. Said procedural steps are also utilized to form the cermet-containing conducting element green compact. In this context, one embodiment provides the powder, which is compressed into the conducting element green compact, to be cermet-containing or to consist of a cermet. Subsequently, the two green compacts—the base body green compact and the conducting element green compact—are combined. After this step, which is called step c), the two green compacts are connected, for example by subjecting them to firing—which is also called sintering. Alternatively, other processes can be applied to connect the two elements, for example gluing, soldering or welding of the elements.

In the firing process, the green compacts are subjected to a heat treatment below the melting temperature of the powder particles of the green compact. This leads to a substantial reduction of the porosity and volume of the green compacts. The special feature of the method thus is that the base body and the conducting element are sintered jointly. There is no longer a need to connect the two elements after this step. Through the firing process, the conducting element becomes connected to the base body in a positive fit-type and/or non-positive fit-type and/or firmly bonded manner. This achieves hermetic integration of the conducting element into the base body. There is no longer a need for subsequent soldering or welding of the conducting element into the base body. Rather, through the joint firing and the utilization of a cermet-containing green compact, a hermetically sealing connection between the base body and the conducting element is attained.

One refinement of the method according to one embodiment is characterized in that step a) includes a partial sintering of the base body green compact, as has been mentioned above. The green compact of the base body is heat-treated in the scope of said partial sintering. This is already associated with some shrinkage of the volume of the base body green compact. However, the volume of the green compact does not reach its final state. Rather, this requires another heat treatment in the scope of step d), in which the base body green compact and the conducting element green compact are shrunk to their final size. In the scope of said variant of an embodiment, the green compact is heat treated only partly in order to already attain a certain surface hardness to render the base body green compact easier to handle. This is expedient for example, in the case of insulating compositions of materials which can be compressed into a green compact shape only with some difficulty.

Another variant of the embodiment is characterized in that the conducting element green compact is also already partly sintered in step b). As described above for the base body green compact, the conducting element green compact can also be partly sintered in order to already attain a certain surface stability. It needs to be noted in this context that the final complete sintering occurs no earlier than in step d). Accordingly, the conducting element green compact attains its final size only in step d).

FIG. 1 illustrates for exemplary purposes an implantable device 100, such as, for example, a cardiac pacemaker, that has an electrical bushing 10 integrated into its metallic housing. The electrical bushing 10 is connected to the housing 110 of the implantable device 100 in a hermetically sealed manner, in one embodiment through welding. It is therefore advantageous in one embodiment that a holding element 20 of the electrical bushing 10 includes a metal that can be welded to the housing 110 easily and reliably. The purpose of the electrical bushing 10 is to establish an electrical connection between the hermetically sealed interior of the medical device 100 and the exterior. Accordingly, a conducting coil 120, which is only indicated schematically here and is connected to a stimulation electrode, can be connected to the electrical bushing 10. Stimulation electrodes of this type are inserted, for example, in heart muscles to allow signals of the cardiac pacemaker to be conducted to the muscle. In order to attain hermetic sealing, the conducting wire 30 is embedded in a base body 40. The base body 40 leads to the formation of a hermetic seal between the holding element 20 and the at least one conducting wire 30 in a through opening 22 formed by the collar-like holding element 20. The electrically insulating base body prevents electrical short-circuiting to occur between the electrically conductive elongated conducting wire 30 and the metallic housing 110 and/or the metallic holding element 20.

In electrical bushings according to the prior art, a metallic wire is used as conducting element and needs to be soldered into a base body 40. For this purpose, the base body 40 includes a cylinder-like bushing for the conducting element 30, with the internal wall of said bushing being provided with a metallic coating. The soldering has proven to be error-prone and expensive. FIG. 2 illustrates an electrical bushing 10 according to one embodiment that overcomes at least one of the disadvantages mentioned above. The electrical bushing 10 includes a collar-like holding element 20. The holding element 20 serves to hold the electrical bushing 10 in the implantable medical device 100. The holding element 20, designed to be collar-like, includes a through-opening 22. This is particularly evident from FIG. 3, which illustrates a top view onto the electrical bushing 10 illustrated in a section in FIG. 2. Designed rectangular in shape and collar-like, the holding element 20 possesses, on its interior, the through-opening 22, which is designed to be rectangular in the present case. At least one elongated conducting element 30 extends through said through-opening 22. In the exemplary embodiment illustrated, a total of five conducting elements 30 extend through the holding element 20. A base body 40 is arranged in the through-opening 22 in such a manner that hermetic sealing is effected between the holding element 20 and the conducting element 30. The special feature according to one embodiment of the electrical bushing 10 illustrated results from the conducting element 30 comprising a cermet or consisting of a cermet.

A cermet is a composite material made of ceramic materials in a metallic matrix. The special feature of a cermet-containing conducting element 50 of this type is that it can be sintered jointly with the base body 40, which is also ceramic-containing, in a single procedural step. Thus, no undesirable through-openings, fissures or imperfections arise any longer between conducting element 50 and base body 40. Rather, a media-tight connection is created between the two elements 40,50. The individual procedural steps for the manufacture of the electrical bushing 10 according to one embodiment are as follows:

a. generating a base body green compact for a base body (40) from an insulating composition of materials;

b. forming at least one cermet-containing conducting element green compact for a conducting element (30);

c. introducing the at least one conducting element green compact into the base body green compact;

d. connecting the base body green compact to the at least one conducting element green compact in order to obtain a base body (40) having at least one conducting element (30).

The special feature according to the scope of the method according to one embodiment results from both the base body green compact and the conducting element green compact each being compressed from powders and then subjected to firing. Accordingly, in just a few procedural steps a green compact can be generated that includes both the conducting element green compact and the base body green compact, and said total green compact is then subjected to firing. In one variant of the embodiment, not only the base body 40 and the conducting element 30, but the holding element 20 also, are compressed from powders and sintered. Accordingly, the holding element 20 is also produced from a cermet-containing powder in one production step. Subsequently, the three green compacts—holding element 20, conducting element 30, base body 40—are joined. This results in the electrical bushing 10 in a green compact stage. Subsequently, the green compacts are jointly subjected to firing. The resulting electrical bushing 10 not only meets all necessary electrical requirements, but it also is produced in one step without any need for subsequent soldering or welding of individual elements. Moreover, the metal-containing, a cermet containing holding element 20 enables a simple durable connection to the housing of the implantable medical device 100 to be established.

FIG. 4 again illustrates a magnification of the individual components of the electrical bushing 10. This magnified detail corresponds to the region denoted I in FIG. 3. Made from an electrically insulating composition of materials, the base body 40 surrounds the conducting element 30. Conducting coils, for example for a cardiac pacemaker, can be connected to said conducting element 30. The base body 40 is surrounded by a holding element 20 that is designed to be collar-like in shape. Said holding element 20 is cermet-containing in the variant of the embodiment illustrated. Consequently, the holding element can be subjected to firing or sintering jointly with the cermet-containing bearing element 50 and the electrically insulating base body 40 in one step. In one embodiment, the holding element 20 and the bearing element 50 are made of the same material in this context.

For integration of the electrical bushing 10 into the implantable medical device 100, the holding element 20 can include a flange. A flange of this type has not been sketched-in in the figures. A housing 110 of the device 100 can touch against the flange in order to enable a hermetically sealing connection of the two elements. In one embodiment, the holding element 20 and the flange are made of the same material and/or as a single part.

Figure 5:
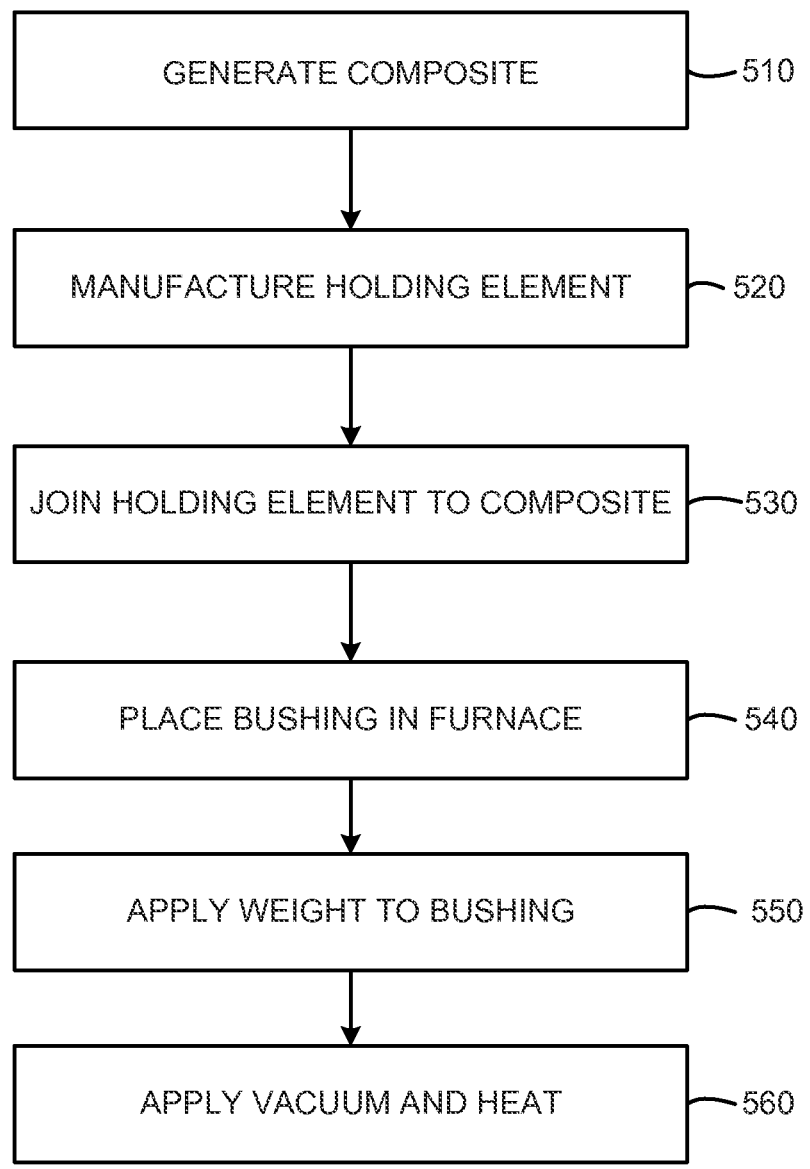
FIG. 5 illustrates a sketch of the procedural steps involved in the manufacture of an electrical bushing having a holding element.

FIG. 5 schematically illustrates the flow of a method for connecting the holding element 20 to the base body 40. In the first step 510, a composite of a base body 40 and a conducting element 30 is generated, as has been done above. Subsequently or concurrently, a holding element 20 is manufactured by turning, milling or metal injection molding in a second step 520. The holding element can be manufactured from a variety of materials. In one embodiment, it is manufactured from a metal. The holding element 20 can be selected, for example, from the group consisting of niobium (Nb), iron (Fe), titanium (Ti), platinum (Pt), iridium (Ir), molybdenum (Mo), tantalum (Ta), tungsten (W), cobalt-chromium alloys or zirconium (Zr) and two thereof. It is also conceivable to use an alloy made from any of the metals listed above and one of the other metals from the group or another metal. The holding element 20 is in one embodiment made from niobium or a niobium alloy.

Figure 9:
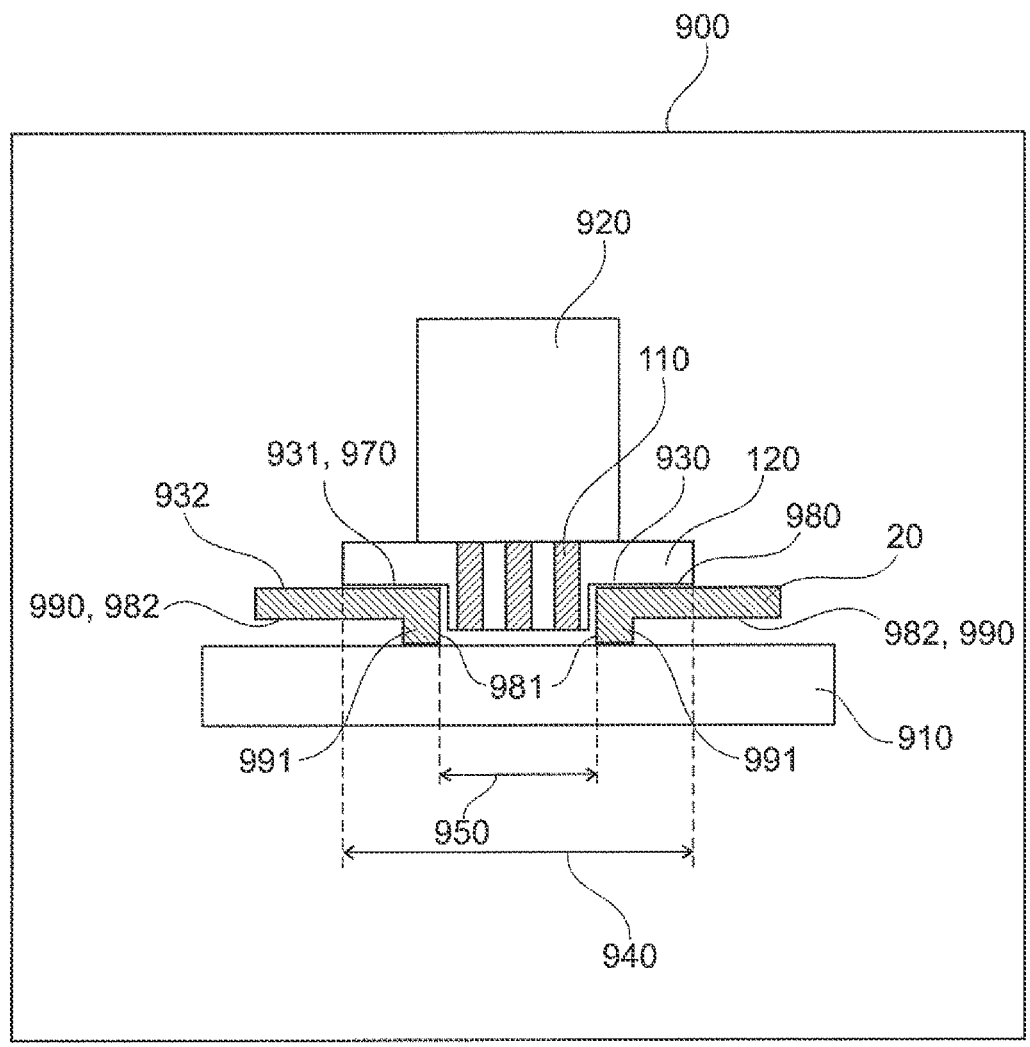
FIG. 9 illustrates a sketch of a bushing having a holding element in a furnace.

The holding element 20 is joined to the composite of base body 40 and conducting element 30 in a third step 530 to form a bushing 10, as is illustrated in FIG. 9. In the process, one contact surface 970 of the base body 40 each and one contact surface 980 of the holding element 20 contact each other. The bushing 10 is placed on a base plate 910 of a heatable furnace 900 made by Degussa, Germany, in a fourth step 540, as is also illustrated in FIG. 9. In a fifth step 550, a weight 920 is applied to the bushing 10. Said step 550 can be carried out either before or after step 540. The size and mass of the weight 920 depend on the size of the bushing 10 and the contact pressure onto the boundary surface between base body 40 and holding element 20 that is to be attained. In the example illustrated, the mass of the weight 920 was approx. 1,000 g. However, it is also conceivable to select the mass of weight 920 to be higher or lower. In one embodiment, the mass is in a range between 100 and 5,000 g, in one embodiment, in a range between 500 and 2,000 g.

The contact pressure exerted by weight 920 weighing 1,000 g depends on the size and geometry of the bushing 10 and holding element 20. In the example illustrated here, the external diameter 940 of the base body 40 of the bushing 10 is approx. 3.5 mm and the internal diameter 950 of the holding element 20 is 2.6 mm. Due to the T-shaped geometry of the bushing 10 in this example, the bottom side 931 of the T crossbar of the bushing 10 is thus pressed onto the top side of the ring-shaped holding element 20 in order to form a joined connection 930. This generates a boundary surface of approx 4.3 mm² between base body 40 and holding element 20. The contact pressure in this case is approximately 2 MPa. Said pressure can be varied through suitable selection of the mass of the weight 920 or of the geometry of the contact surface of bushing 10 and holding element 20. In one embodiment, the contact pressure in this context is selected to be in a range from 0.5 to 10 MPa. The contact pressure is the sum of the pressure exerted by the weight onto the joined connection 930 of base body 40 and holding element 20 and the negative pressure existing in the furnace 900.

After placing the bushing 10 with holding element 20 and the weight 920 into the furnace 900, a vacuum is applied to the furnace 900 in the sixth step 560 and the furnace 900 is heated to 1,700° C. for 2 hours. In this context, the temperature can either be constant or vary. In one embodiment, the temperature in the furnace 900 is between 800 and 2,200° C., in one embodiment between 1,100 and 1,800° C., during the 1 to 4 hour duration of the process. The pressure during the duration of the process is 0.2 to 20 MPa. The pressure can also be varied. In one embodiment, the pressure in the furnace 900 is between 1 and 1 MPa. Moreover, it is preferred in one embodiment that a negative pressure, in one embodiment of less than $1*10^{-4}$ mbar, exists in the furnace 900 during the connecting.

In order to attain a particularly durable and rapid connection to form between bushing 10 and holding element 20, the contact surfaces 970 of the bushing 10 and the contact surface 980 of the holding element 20 can be processed in the first step 510 prior to the joining. Said processing can, for example, involve polishing or grinding. Accordingly, it is advantageous in one embodiment to select a roughness of the surfaces 970 and 980 such that a mean roughness is less than 1 μm, in one embodiment less than 0.5 μm, in one embodiment less than 0.1 μm, and in one embodiment less than 0.01 μm. By this means, the diffusion bonding process proceeding in the furnace 900, can be supported such that a connection between bushing 10 and holding element 20 is durably provided, for example for several years, in one embodiment for several decades.

Figure 6:
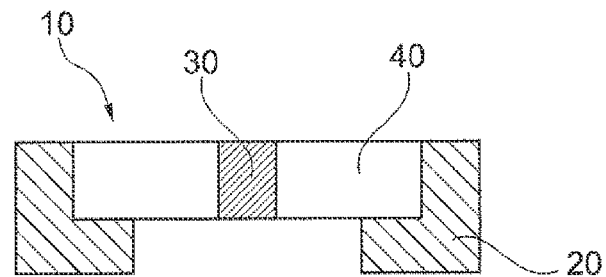
FIG. 6 illustrates a sketch of a rectangular bushing surrounded by a holding element.
Figure 7:
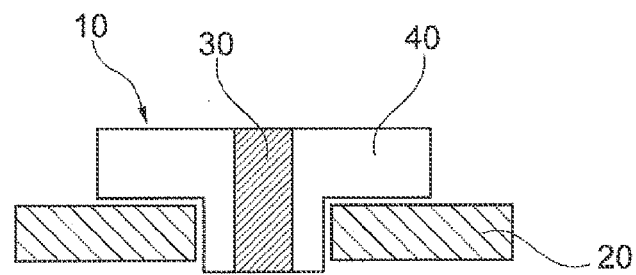
FIG. 7 illustrates a sketch of a T-shaped bushing surrounded by a round holding element.

FIGS. 6 and 7 illustrate various geometries of bushing 10 and holding element 20. Accordingly, bushing 10 of FIG. 6 includes a cermet-containing conducting element 30 that is surrounded by insulation material, which forms a base body 40 around the conducting element 30. The bushing 10 formed in this example is rectangular in shape. However, any other shape, such as round, triangular shapes, are conceivable as well such that the bushing can take the shape of a sphere or cube or cylinder or cone or any other three-dimensional shapes. In this context, the holding element 20 surrounds at least a part of at least one external surface of the bushing 10. In this example, the holding element 20 has an L-shaped cross-section such that the base body 40 can contact the contact surface 980 of the holding element 20 through a contact surface 970 on one of the internal surfaces of the L shape. A positive fit-type connection can thus be formed through said contact surfaces. The function of the holding element 20 in this context is to effect a simple connection to a housing of a medical device, into which the bushing 10 is to be introduced. This ensures that the housing of the medical device is hermetically sealed by the bushing 10 with the aid of the holding element 20. Since the holding element 20 is at least partly made of metal, said connection to the housing can be effected, for example, through soldering or welding. Alternatively, gluing processes are feasible just as well.

In FIG. 7, the cross-section of the bushing 10 has a T-shape. In this context, a cermet-containing conducting element 30 is arranged in the stem of the T such that the conducting element 30 is surrounded on both sides by an L-shaped insulation layer in the form of a base body 40. In a three-dimensional view, the conducting element 30 is surrounded in a ring-shape by the base body 40, whereby the diameter of the ring decreases incrementally from one side of the conducting element 30 to the other end. The purpose of the increment is to form a level contact surface 970 on the base body 40 transverse to the orientation of the conducting element 30 within the base body 40 that enables contact to a contact surface 980 of the holding element 20. Due to the horizontal orientation of said contact surfaces 970 and 980, a weight 920, as illustrated in FIG. 9, can be used to facilitate a positive fit to form between bushing 10 and holding element 20.

Figure 8:
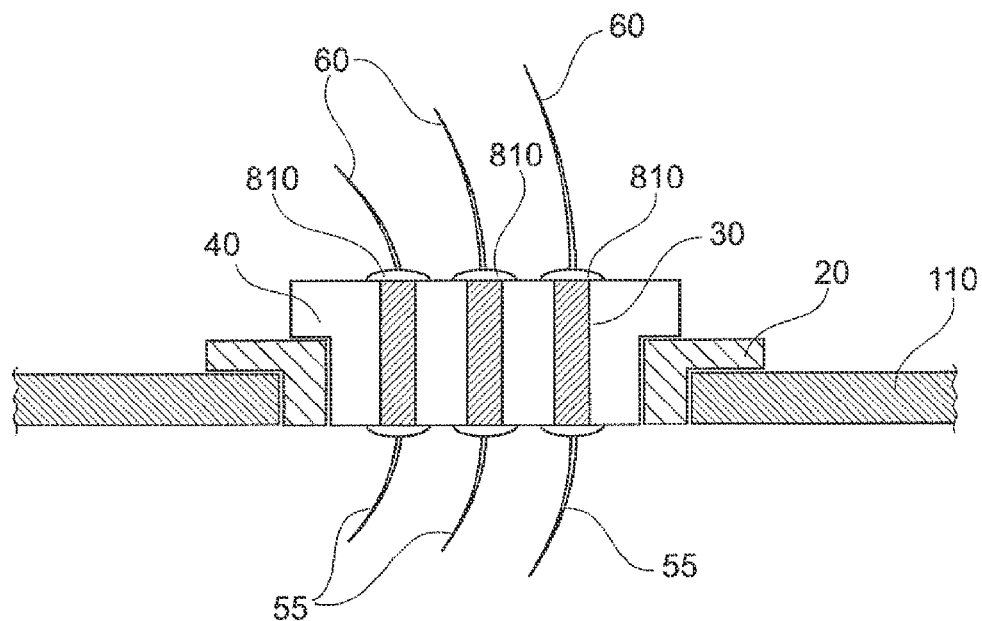
FIG. 8 illustrates a sketch of a T-shaped bushing surrounded by holding elements, having multiple contacted cermet conducting elements, incorporated into a housing of a medical device.

FIG. 8 illustrates a bushing with holding element 20 and three conducting elements 30 that are contacted through wires 55 and 60 and are incorporated into a housing 110 of a medical device that is not illustrated here. In this context, the internal wires 60 point to the inside of the device, whereas the external wires 55 enable the contacting to an external device or a tissue. The wires 55, 60 are connected to the cermet-containing conducting elements 30 through a contact surface 810.

FIG. 9 illustrates a furnace 900 that is filled by placing a bushing 10 on its floor plate 910. The bushing 10 contacts a holding element 20 and a weight 920 on the furnace's bottom side 931 and top side 932, respectively. The weight 920 increases the pressure between the bushing 10 and the holding element 20 under the bushing. As has been described in FIG. 5, said furnace can be temperature-controlled and pressure can be applied such that the elevated pressure acting on the joined connection 930 having the contact surfaces 970 and 980 enables fusion of the materials of the bushing 10 and holding element 20. In this example, the holding element 20 has an L-shaped cross-section. This not only generates a large contact surface 980 to the bushing 10, but also two more surfaces 981 and 982, for example as contact surfaces 990, 991, for contacting a housing of a medical device (not illustrated here).

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for the manufacture of an electrical bushing for an implantable medical device, the method comprising:
   a. generating at least one base body green compact for at least one base body from an insulating composition of materials;
   b. forming at least one cermet-containing conducting element green compact for at least one conducting element;
   c. introducing the at least one conducting element green compact into the base body green compact;
   d. connecting the base body green compact to the at least one conducting element green compact in order to obtain at least one base body having at least one conducting element;
   wherein the base body is connected to a holding element, the holding element consisting at least in part of metal, via a diffusion bond formed at a temperature between 100° C. and 3,000° C., and wherein a pressure acting on a connecting site between base body and holding element while the diffusion bond is formed between the holding element and the base body, said pressure in a range from 0.2 to 20 MPa.

2. The method according to claim 1, wherein the metal is selected from the group consisting of a metal from any of the subgroups IV, V, VI, VIII, IX, and X of the periodic system of the elements or at least two thereof.

3. The method according to claim 2, wherein the metal is selected from the group consisting of platinum, iron, iridium, niobium, molybdenum, tantalum, tungsten, titanium, cobalt, chromium, and zirconium, or at least two thereof.

4. The method according to claim 1, wherein the holding element includes niobium and
wherein the base body includes a zirconium oxide.

5. The method according to claim 1, wherein the holding element includes a material selected from the group consisting of niobium, platinum, iron, and molybdenum, or at least two thereof, and
wherein the base body includes an aluminum oxide.

6. The method according to claim 1, wherein the base body green compact is subjected to firing jointly with the at least one conducting element green compact.

7. The method according to claim 1, wherein step a) comprises a partial sintering of the base body green compact.

8. The method according to claim 1, wherein step b) comprises a partial sintering of the conducting element green compact.

9. A method for the manufacture of an electrical bushing for an implantable medical device, the method comprising:
   a. generating at least one base body green compact for at least one base body from an insulating composition of materials;
   b. forming at least one cermet-containing conducting element green compact for at least one conducting element;
   c. introducing the at least one conducting element green compact into the base body green compact;
   d. connecting the base body green compact to the at least one conducting element green compact in order to obtain at least one base body having at least one conducting element;
   wherein the base body is connected to a holding element via a diffusion bond formed at a temperature between 100° C. and 3,000° C.; and
   wherein either step a) comprises a partial sintering of the base body green compact or step b) comprises a partial sintering of the conducting element green compact such that one of the base body green compact and the conducting element green compact is easier to handle.

* * * * *